United States Patent [19]

Blom et al.

[11] 4,442,349

[45] Apr. 10, 1984

[54] CIRCUITRY FOR THE GENERATION AND SYNCHRONOUS DETECTION OF OPTICAL PULSED SIGNALS

[75] Inventors: Sture R. Blom, Wayland; Theodore M. Osborne, Burlington, both of Mass.

[73] Assignee: Baird Corporation, Bedford, Mass.

[21] Appl. No.: 187,518

[22] Filed: Sep. 15, 1980

[51] Int. Cl.³ ............................................. G01J 3/00
[52] U.S. Cl. ................................ 250/222.1; 250/343; 356/316; 356/326
[58] Field of Search ............ 250/221, 222 R, 343–345; 356/315, DIG. AAS, 316, 326

[56] References Cited

U.S. PATENT DOCUMENTS 3,645,629 2/1972 Dagnall ................................ 356/315
3,678,269 7/1972 Malek ............................. 250/343 X
3,805,074 4/1974 McCormack .................... 250/343 X
3,825,344 7/1974 Bonne ..................... 356/DIG. AAS
4,029,957 6/1977 Betz et al. .................... 250/222 R X
4,061,918 12/1977 Prier et al. .......................... 250/343

Primary Examiner—David C. Nelms
Assistant Examiner—Edward P. Westin
Attorney, Agent, or Firm—Morse, Altman & Dacey

[57] ABSTRACT

Circuitry for the generation and synchronous detection of optical pulsed signals contaminated by additive background noise characterized by a high signal-to-noise ratio. The circuitry comprises a source for generating optical pulsed signals, a detector for generating detector signals in response to the optical pulsed signals, and a signal processor for processing the detector signals in synchronism with the optical pulsed signals. The signal processor for processing the detector signals includes a high pass filter, an integrator and at least one switch synchronized with the optical pulsed signals for driving the integrator. The circuitry is preferably under computer control.

3 Claims, 5 Drawing Figures

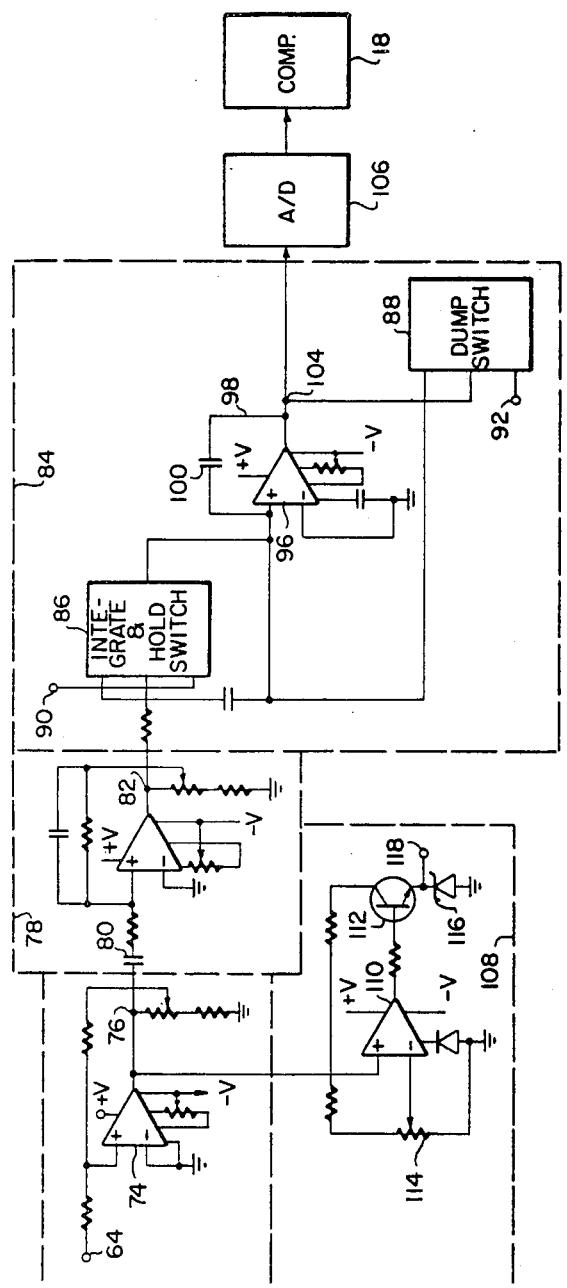
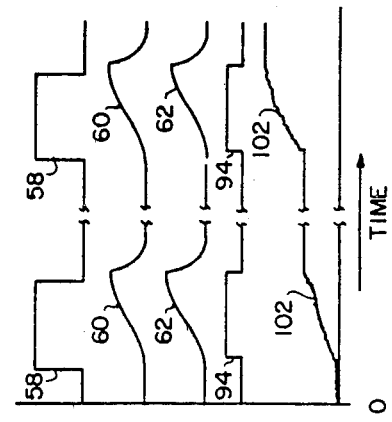
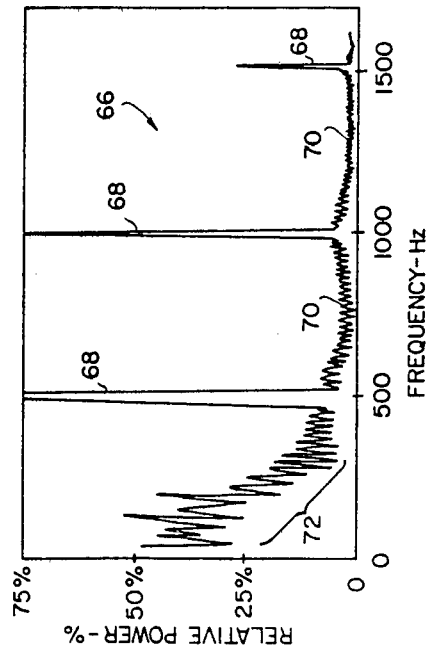

CIRCUITRY FOR THE GENERATION AND SYNCHRONOUS DETECTION OF OPTICAL PULSED SIGNALS

BACKGROUND OF THE INVENTION

1. Field of the Invention

The present invention relates generally to pulsed signal circuitry and, more particularly, to a circuitry for the generation and synchronous detection of optical pulsed signals contaminated by a large additive background noise characterized by a high inherent signal-to-noise ratio.

2. The Prior Art

Various types of spectrometers have been used over the past several decades for the spectrochemical analysis of unknown elements in a sample solution. For instance, in an atomic absorption spectrometer, an excitation source such as a hollow cathode lamp is employed to excite the sample atoms. The spectrometer then measures the radiation absorbed by these sample atoms so as to determine their concentration within the sample. In atomic and fluorescent emission spectrometers, it is the intensity of the emitted characteristic radiation that is measured and related to the concentration of the particular element in the sample. All of these, as well as others, such as spark-gap spectrometers encounter a problem of noise contamination. This problem of noise contamination is particularly acute when analyzing a sample containing a plurality of unknown elements. The problem is further complicated in atomic fluorescence spectroscopy by the fact that unwanted thermally excited emission also occurs at the same wavelength as fluorescent emission.

Additive noise contamination is essentially of two kinds:

(a) noise characterized by having a relatively constant value over a wide range of frequencies, known as white-frequency spectrum noise, and (b) noise whose value changes inversely with frequency, known as excess low frequency noise since it primarily occurs at the lower end of the frequency spectrum, and is also referred to as 1/f frequency spectrum noise.

In order to have a reliable, accurate spectrometer with an acceptable detection limit, the spectrometer must have a good output signal-to-noise ratio. In order to achieve such a good output signal-to-noise ratio, most if not all noise contamination (i.e., extraneous noise) must be eliminated from the desired signal. Furthermore, the manner employed to eliminate the extraneous noise should be simple, reliable and having a useful life at least coterminous with that of the spectrometer in which it is incorporated. Thus, extraneous noise elimination involves difficult complexities. Since elimination of the noise at the source is seldom if ever possible, some kind of signal processing that reduces the extraneous noise is needed. Presently available techniques at noise attenuation have been wanting for either not doing an adequate job or being too cumbersome, hence expensive. Thus, there is a need for a fresh approach to eliminate extraneous noise when working with pulse type signals.

SUMMARY OF THE INVENTION

It is a principal object of the present invention to overcome the above disadvantages by providing circuitry for the generation and synchronous detection of pulsed signals contaminated by additive background noise.

More specifically, it is an object of the present invention to provide circuitry comprising means for generating optical pulsed signals, means for generating detector signals in response to the optical pulsed signals, and means for processing the detector signals in synchronism with the optical pulsed signals. Preferably, the means for processing the detector signals includes a high pass filter, an integrator, at least one switch synchronized with the optical pulsed signals for driving the integrator, and an overload detector coupled to the means for generating optical pulsed signals.

Other objects of the present invention will in part be obvious and will in part appear hereinafter.

The invention accordingly comprises the circuitry of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein:

FIG. 3 is a also a detailed schematic but of another portion of the circuitry of FIG. 1;

FIG. 4 is a graph of a typical detector noise spectrum; and

FIG. 5 illustrates signal processing in the circuitry of FIG. 1.

DETAILED DESCRIPTION OF THE PREFERRED EMBODIMENT

Figure 1:
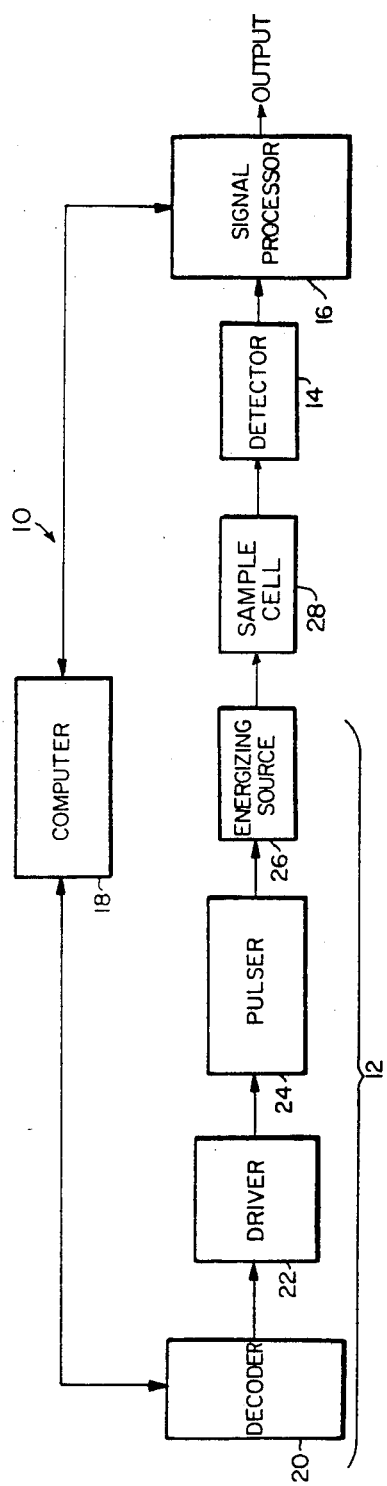
FIG. 1 is a general schematic of a circuitry embodying the present invention.

Generally, the illustrated embodiment of a circuitry 10 for the generation and synchronous detection of pulsed signals comprises means 12 for generating optical pulsed signals, means 14 for generating detector signals responsive to the optical pulsed signals, and means 16 for processing the detector signals in synchronism with the optical pulsed signals. The circuitry 10 is preferably under the control of a computer 18.

The means 12 for generating optical pulsed signals preferably includes a decoder 20 to interface with the computer 18, a driver 22 for generating a series of variable analog signals, a pulser 24 for generating current pulses, and an optical energizing source 26 for generating optical pulsed signals. The optical pulsed signals emanating from the energizing source 26 are preferably directed at a sample cell 28 containing unknown elements whose respective concentrations are to be measured by some system of which the circuitry 10 of the invention forms a component part. The optical pulsed signals, either absorbed by, passing through, emitted by or reflected from the sample cell 28, are then detected by an optical detector 14. The detector signals generated by the optical detector 14 in response to the optical pulsed signals then are processed by the signal processor 16 in synchronism with the optical pulsed signals. In the case where the sample cell 28 is also an ionizing source with fast temporal response (such as an inductively coupled plasma), the computer 18 can be used to change the strength of power of the ionizing source in synchronism with the optical pulsed signals to maximize the output signal-to-noise ratio for a given element in a given matrix.

Figure 2:
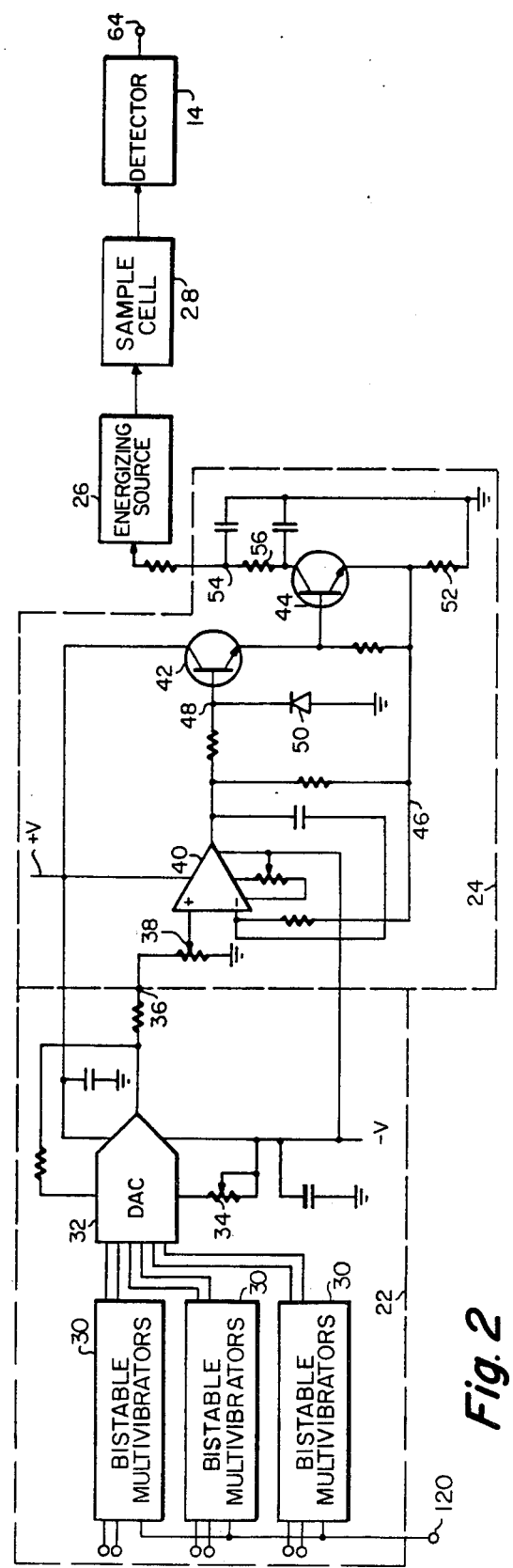
FIG. 2 is a more detailed schematic of a portion of the circuitry of FIG. 1.

FIG. 2 is a more detailed schematic view of a portion of the circuitry 10 of FIG. 1. FIG. 2 depicts in some detail the construction of the driver 22 and of the pulser 24. The demultiplexed signals from the decoder 20 are coupled to a plurality (three being illustrated) of bistable multivibrators 30 whose outputs are fed to a digital-to-analog converter (DAC) 32. A variable resistor 34 allows the DAC 32 to generate a series of variable analog signals at its output 36. These series of analog signals preferably are variable over a range of zero to five volts d.c., and represent a preferred selectable range of one of sixty-four steps of analog signals achievable at the DAC output 36. The significance of this selectable range in the series of analog signals will be apparent from the description below.

The series of analog signals appearing at the output 36 of the DAC 32 are coupled to the pulser 24 via a potentiometer 38. The pulser 24 essentially includes a summing operational amplifier (Op Amp) 40 and a pair of NPN transistors 42 and 44 connected in a Darlington configuration. The series of analog signals from the output 36, and via the potentiometer 38, represent one of the inputs to the Op Amp 40, with the other input being represented by a negative feedback loop 46 connected to a current viewing resistor 52 and the emitters of the pair of transistors 42 and 44. The output 48 of the Op Amp 40 is connected to the base of the first NPN transistor 42, and with positive signals emanating from the output 48, the transistor 42 is rendered conductive. A clamping diode 50 is shown also connected between the output 48 and ground so as to clamp any negative signal excursions appearing at the output 48 to ground. It is apparent that, absent the clamping diode 50, such negative signal excursions, if of sufficient magnitude, would make the transistor 42 again to non-conducting. The transistor 42 drives the transistor 44 by having the emitter of the transistor 42 connected to the base of the second NPN transistor 44. The transistor 44 is preferably a high energy, power transistor designed to handle high current and power. The current viewing resistor 52 is connected between the emitter of the power transistor 44 and ground, thereby supplying a negative feedback signal proportional to the output current. Because of the high gain around the negative feedback loop 46, the output current pulses are an accurate replica of the analog signals at the output 36 of the DAC 32. The output current pulses of the pulser 24 appearing at its output 54 are taken from the collector of the power transistor 44 across a dissipating resistor 56. The dissipating resistor 56 dissipates some of the power generated and thus serves to protect the power transistor 44.

The pulser 24, in response to the series of variable analog signals generated by the driver 22, thus produces at its output 54 a train of current pulses 58 (observe FIG. 5) used to activate the energizing source 26. These current pulses 58 are characterized by a rapid response rise time measured in microseconds so as to result in a clean, fast rise current pulse. Further, the current pulses 58 maintain their near ideal square-wave shape per unit of time regardless of variations in the load represented by the energizing source 26. The height of the current pulses 58, representing the amount of current delivered per each current pulse 58 to the energizing source 26, depends upon the particular selected level of the series of variable analog signals appearing at the output 36 of the DAC. It will be recalled that, with the aid of the variable resistor 34, the series of analog signals can be selected between a range of zero level and up and through sixty-four steps, encompassing a voltage range of zero to five volts d.c. It is to be noted that an upward adjustment of but one level in the series of analog signals causes the height and hence the amount of the current pulses 58 to be increased by a factor of about 1.2. With greater amount of current being delivered to the energizing source 26, its pulsed optical energy output 60, i.e., the intensity of illumination, will also increase correspondingly. The energizing source 26 can be a spark-gap, a laser, a hollow cathode lamp, or the like, depending on the particular system employed of which the circuitry 10 is a part. It is to be also noted that the duration of the current pulses 58 determines the time interval during which the energizing source 26 is on, i.e., the length of its corresponding pulsed optical energy output signal 60, note FIG. 5. The pulsed optical energy output signals 60 are somewhat delayed in time from the current pulses 58 and are not square waves either. The detector 14 in turn generates a plurality of detector output signals 62 at its output 64 which follow closely the pulsed optical energy output signals 60 as regards shape, duration and timing. Each of these detector output signals 62 includes extraneous noise in addition to the desired signal. The extraneous noise essentially represents the d.c. component of the detector output signal 62 and the desired signal represents the a.c. component of the detector output signal 62.

A graph 66 of a typical detector noise spectrum is shown in FIG. 4, which plots the graph's 66 relative power, in terms of percentages, against the frequency of its output in Hertz. The graph 66 includes a number of spikes 68 at 500 Hz and harmonics thereof, representing the pulse character of the desired signal. The graph 66 also includes extraneous noise, i.e., the d.c. component, that is basically composed of two kinds of additive background noise. One kind of additive background noise 70 is characterized by possessing a near constant value above some characteristic frequency, such as about 500 Hz, and is also referred to as "white-frequency spectrum" noise. The second kind of additive background noise 72 is characterized, in contrast to noise 70, by possessing a higher and rising value below this characteristic frequency, herein about 500 Hz. This second kind of additive background noise 72 is also known as excess low frequency (ELF) noise or 1/f spectrum noise. In order for the circuitry 10 to possess a high signal-to-noise ratio, this 1/f spectrum noise 72, the low frequency component of the detector output signal 62, must be attenuated before the detector output signal 62 is integrated. This is one of the functions of the signal processor 16.

FIG. 3 depicts a detailed schematic of the signal processor 16. The detector output 64 also represents the input to the signal processor 16. The detector output signals 62 appearing at the detector outputs 64 can be either current signals or voltage signals, depending upon the particular type of optical detector 14 employed in the overall system of which the circuitry 10 is but a component part. Consequently, the first operative component of the signal processor 16 is represented by a wide band d.c. amplifier 74 which functions either as a current to voltage converter and amplifier or simply as a voltage to voltage amplifier, depending on the nature of the detector output signals 62 coupled to the wide band d.c. amplifier 74. The output 76 of the wide band d.c. amplifier 74 is coupled to a high pass filter 78, which includes a d.c. blocking capacitor 80. It is the function of this high pass filter 78 to attenuate the extraneous noise, particularly the ELF or 1/f spectrum noise 72, from the detector output signals 62 as appearing at the output 76 of the wide band d.c. amplifier 74. Due to this attenuation of this type of extraneous noise from the detector output signals 62, the signal-to-noise ratio of the circuitry 10 has been brought to its highest attainable level. Consequently, the detector output signals 62 appearing at the output 82 of the high pass filter 78 carry mostly the desired signal as represented by the spikes 68, i.e., the a.c. component of the detector output signals 62.

An integrator network 84 comprises the next component part of the signal processor 16. This integrator network 84 is designed to function in one of three modes: an integrate mode, a hold mode or a dump (reset) mode. The selection of the particular mode for the integrator network 84 is effected by a pair of analog electronic switches 86 and 88. The switch 86 incorporates the function for the selection of either the integrate or the hold modes, and switch 88 functions but as a dump switch. Commands to the switches 86 and 88 in the form of voltage pulses are initiated by and from the computer 18 and conveyed to the switches 86 and 88 via leads 90 and 92, respectively. The commands to the integrate and hold switch 86 via lead 90 are in the nature of gate voltage pulses 94 (observe FIG. 5) synchronized with the optical energy output pulses 60. The switch 86 drives an operational amplifier 96 in whose feedback loop 98, an integrating capacitor 100 is found. Consequently, the detector output signals 62, now attenuated by the high pass filter 78 and appearing at its output 82, are coupled by switch 86 to the operational amplifier 96 and are integraed at the integrating capacitor 100 for the duration of the gate voltage pulses 94 as analog integrating increments 102. During the time interval in between the gate voltage pulses 94, the switch 86 is in its hold mode, ensuring that the successive analog integrating increments 102 are held by the integrating capacitor 100. The gated integration continues for a preselected number of optical energy output pulses 60, following which the level of the analog integrating increments 102 appearing at the output 104 of the integrator network 84 is sampled by an analog to digital converter (A/D) 106 before being fed to the computer 18. After the sampling, the dump switch 88 resets the integrating capacitor 100 to zero on command of the computer 18 in the form of an appropriate voltage pulse and coupled to the switch 88 via the lead 92. It should be noted that the operational amplifier 96 also functions as a buffer amplifier to isolate the integration proceeding on the integrating capcitor from load variations.

The signal processor 16 preferably also incorporates an overload detector 108 coupled to the output 76 of the wide band d.c. amplifier 74. The overload detector 108 includes an amplifier 110, an NPN transistor 112 whose collector is connected in a feedback loop of the amplifier 110 via a threshold-setting potentiometer 114, and a zener diode 116 connected between the emitter of the transistor 112 and ground. The output 118 of the overload detector 108 in turn is coupled to an input lead 120 of the driver 22 (note FIG. 2) and thereby to each of the plurality of multivibrators 30. The overload detector 108 is basically a comparator which compares the level of the detector output signals 62 appearing at the output 76 of the wide band d.c. amplifier 74 with the set threshold level at the threshold-setting potentiometer 114. If the former exceeds the latter, overload detector 108 produces an overload signal at its output 118 and couples this overload signal to each of the multivibrators 30 via the input lead 120. The arrival of the overload signal at the multivibrators 30 causes the multivibrators 30 to become disabled. The disabled multivibrators 30 in turn cause the DAC 32 to cease the further generation of the series of variable analog signals, and hence the generation by the pulser 24 of the train of current pulses 58. In the absence of such current pulses 58, the energizing source 26 ceases the generation of its pulsed optical energy output 60. This condition is maintained until the overload signal is eliminated at the output 118 of the overload detector 108.

The output of the overload detector 108 could alternately be connected to the computer 18 so as to allow the computer to disable the multivibrators 30 via the decoders 20.

We have thus shown and described a circuitry 10 for the generation and synchronous detection of pulsed signals, which circuitry 10 is characterized by a high signal-to-noise ratio and thus satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. Circuitry for the generation and synchronous detection of pulsed signals in a spectrometer, said circuitry being characterized by a high signal to noise ratio comprising:
   (a) means for generating current pulses;
   (b) means for generating pulsed energy signals in response to said current pulses;
   (c) means for generating detector signals in response to said pulsed energy signals;
   (d) means for processing said detector signals in synchronism with said pulsed energy signals including an integrator, a switch synchronized with said pulsed energy signals for driving said integrator and a high pass filter to remove extraneous noise in the 1/f frequency spectrum from said detector signals before they are integrated by said integrator;
   (e) a second switch coupled to said integrator for dumping said integrated detector signals; and
   (f) means for generating a series of signals for driving said means for generating current pulses, said series of signals being variable analog signals.

2. The circuitry of claim 1 wherein said means for processing said detector signals further includes a wide band d.c. amplifier to couple said detector signals to said high pass filter and an overload detector coupled to said wide band d.c. amplifier for generating an overload signal coupled to said means for generating current pulses for shutting off the further generation of said current pulses.

3. The circuitry of claim 2 wherein said overload detector includes a comparator circuit comprising an amplifier, a transistor whose base is connected to the output of said amplifier, and a threshold setting potentiometer, with the collector of said transistor being connected in a feedback loop of said amplifier via said threshold-setting potentiometer, and said overload signal being generated at the emitter of said transistor.

* * * * *